United States Patent [19]

Cairati et al.

[11] 4,024,074

[45] May 17, 1977

[54] CATALYST FOR THE OXIDATION OF METHANOL TO FORMALDEHYDE AND PROCESS FOR PREPARING THE SAME

[75] Inventors: Luciano Cairati, Cassano D'Adda Milan; Ferruccio Trifiro, Pierluigi Villa, both of Milan, all of Italy

[73] Assignee: Societa' Italiana Resine S.I.R. S.p.A., Milan, Italy

[22] Filed: Mar. 5, 1976

[21] Appl. No.: 664,199

[30] Foreign Application Priority Data

Mar. 5, 1975 Italy .................................. 20918/75

[52] U.S. Cl. .......................... 252/470; 260/603 HF
[51] Int. Cl.² .......................................... B01J 23/88
[58] Field of Search ............. 252/470; 260/603 HF, 260/603 R

[56] References Cited

UNITED STATES PATENTS

| | | | |
|---|---|---|---|
| 2,812,309 | 11/1957 | Allyn et al. | 252/470 |
| 3,716,497 | 2/1973 | Courty | 252/470 |

Primary Examiner—W. J. Shine
Attorney, Agent, or Firm—Jay L. Chaskin

[57] ABSTRACT

A catalyst active and selective in the oxidation of methanol to formaldehyde is prepared by mixing an aqueous molybdate solution with an aqueous solution of a ferric salt, while maintaining a Mo/Fe atomic ratio of from 1.6:1 to 2.2:1 in the mixture, heating the resulting suspension at 70°–100° C for at least 30 minutes, washing the resulting precipitate with water, drying said precipitate to reduce its water content to 2–8% by weight, reducing the dried precipitate to granules and drying the latter to completely remove water, impregnating the dried granules with an aqueous solution of a decomposable bismuth salt and drying and calcining the impregnated granules. The catalyst consists of granules of crystalline iron molybdate and molybdenum trioxide having on their surface an interaction product thereof with bismuth oxide, said molybdenum trioxide and said bismuth being present in an amount of 5–35 wt.% and 0.5–10 wt.%, respectively, with respect to the crystalline iron molybdate.

13 Claims, No Drawings

CATALYST FOR THE OXIDATION OF METHANOL TO FORMALDEHYDE AND PROCESS FOR PREPARING THE SAME

The present invention relates to the production of formaldehyde by catalytic oxidation of methanol. More particularly, the invention relates to a novel catalyst which can be used in fluidized form and which is active and selective for such an oxidation reaction, and a process for the preparation of the catalyst.

In commercially known processes formaldehyde is obtained by dehydrogenation and oxidation of methanol on metallic silver, operating in deficiency of air, or else by oxidation of methanol in a considerable excess of air on metal oxide catalysts, operating at relatively low temperatures (300°–400° C).

The processes which use metal oxides as catalysts have, with respect to those using metallic silver, the advantages of higher yields in formaldehyde and almost complete methanol conversion.

In consequence, one does not need to recover the unaltered methanol from the reaction products and aqueous solutions of formaldehyde which are substantially free of alcohol are obtained.

Moreover, the metal oxide catalysts have a relatively long working life, and because of their selectivity, they permit the production of aqueous solutions of formaldehyde with a very low content of formic acid.

According to the Patent literature, metallic oxides suitable for this purpose are those of molybdenum and iron in which the $MoO_3/Fe_2O_3$ molar ratio may range within wide limits and in general from 3.6:1 to about 11:1.

However, the catalysts used industrially contain a relatively high excess of molybdenum trioxide, since catalysts lacking in this compound show a poor selectivity in the oxidation processes of methanol to formaldehyde.

The preparation of these known catalysts is carried out by:
forming a complex precipitate starting from solutions containing soluble salts of molybdenum and iron,
separating, washing and drying the precipitate,
reducing it to bodies of suitable form and size, and calcining at high temperature.

The calcining treatment, which is usually carried out at temperatures above about 400° C, permits the selectivity shown by the catalysts in the oxidation reaction to be perceptibly improved.

However, the calcining also brings about a decrease in the mechanical characteristics of the catalysts and therefore recourse is made in the art to special expedients, such as processing in the plastic state carried out on the precipitate before drying, or else pelletizing of the precipitate dried and reduced to powder.

These procedures do not allow the production of catalysts which have completely satisfactory mechanical characteristics, or at least the mechanical characteristics are not such as to allow the use of the catalysts in the form of a fluidized bed.

Moreover, the excess of molybdenum trioxide in the catalyst involves drawbacks due to volatilization of this compound, during the oxidation of methanol, in those zones of the catalytic bed where the temperature reaches higher values and the vaporized molybdenum trioxide settles in the cooler zones at the bottom of the bed.

As a result, there is a decrease in the activity and selectivity values in time.

The drawbacks of the prior art are overcome by means of the catalyst of the present invention, active and selective in the oxidation of methanol to formaldehyde and endowed with such mechanical characteristics that it can be used in the form of a fluidized bed in the oxidation reaction.

The catalyst of the present invention is not supported and consists of granules of crystalline iron molybdate $(Fe_2(MoO_4)_3$ and molybdenum trioxide $MoO_3$ in an intimate mixture, said granules having an interaction product thereof with bismuth oxide deposited on their surface. More particularly, the amount of molybdenum trioxide may range from 5 to 35% by weight with respect to the crystalline iron molybdate and is preferably of the order of 19–20% by weight.

Moreover, the amount of bismuth, expressed as metal, may range from 0.5 to 10% by weight and is preferably of the order of 1.5–5% by weight, still with respect to the crystalline iron molybdate.

The process for preparing the catalysts of the present invention comprises the following series of steps:

a. mixing an aqueous solution of a soluble molybdate having a pH value of from 1.05 to 2.8 with an aqueous solution of a soluble ferric salt at a temperature of from 20° to 80° C in such proportions as to ensure in the resulting mixture an atomic ratio of molybdenum to iron of from 1.6:1 to 2.2:1, thereby to obtain a suspension of an amorphous precipitate;

b. heating said suspension for at least 30 minutes at a temperature of from 70° C to its boiling point, thereby to transform said amorphous precipitate into crystalline iron molybdate and molybdenum trioxide;

c. washing the resulting precipitate with water at a temperature of from ambient temperature (20°–25° C) to 100° C to remove the soluble salts produced;

d. drying the washed precipitate at a temperature not exceeding 120° C, thereby to reduce its water content to a value of from 2 to 8% by weight;

e. reducing the dried precipitate to granules and drying said granules at a temperature not exceeding 300° C to completely remove water;

f. impregnating said granules with an aqueous solution of decomposable bismuth salt in such conditions as to ensure an amount of deposited bismuth (expressed as metal) of from 0.5 to 10% by weight with respect to the crystalline iron molybdate;

g. drying said impregnated granules and calcining them at a temperature of at least 300° C for a period of at least 4 hours.

The water-soluble molybdates are preferably alkali metal and ammonium molybdates. Examples of these compounds are: ammonium paramolybdate $(NH_4)_6Mo_7O_{24}.4H_2O$ and ammonium dimolybdate $(NH_4)_2MoO_7.xH_2O$.

The water-soluble ferric salts are preferably ferric nitrate $Fe(NO_3)_3.9H_2O$ and ferric chloride $FeCl_3.6H_2O$.

The soluble molybdate is generally dissolved in water up to a concentration of from 20 to 30 g/l and the pH of the resulting solution is conveniently brought within the above indicated range of values by the addition of a mineral acid, such as nitric or hydrochloric acid.

An aqueous solution of ferric salt is prepared separately by dissolving said salt in water, generally up to a concentration of from 90 to 140 g/l. Preferably, the resulting solution should have a pH value of from 0.5 to 1.5. A possible correction of the pH value may be effected by the addition of a mineral acid.

The two solutions are then mixed and during the mixing the solution of molybdenum salt can be added to that of ferric salt or vice-versa, or else the two solutions can be simultaneously poured into the mixing zone.

In any case, it is convenient to stir the mass, and the temperature is kept at a value of from 20° to 80° C.

The amounts of the two solutions are such as to ensure in the resulting mixture a molybdenum/iron atomic ratio of from 1.6:1 to 2.2:1 and preferably from 1.8:1 to 2.0:1.

By operating in the manner described, the precipitate formed is amorphous or substantially amorphous under X-ray examination, and according to the process of the present invention the suspension thus obtained is heated at a temperature of from 70° C to its boiling temperature for a period of at least 30 minutes and generally not exceeding 6 hours (typically 3-6 hours). In any case, the heating period should be such as to ensure the practically complete conversion of the iron compound (and of the corresponding amount of molybdenum compound) into crystalline iron molybdate.

In this stage of the process, it is possible to add to the suspension of a small amount of a substance capable of promoting the crystalline transformation, such as for example preformed crystalline iron molybdate.

At the end of heating, the suspension is conveniently decanted or else filtered and the residual solid is washed with water, acidulated or not, at a temperature of from 20° to 100° C, to remove the soluble salts which are formed in the reaction between the molybdate and the ferric salt.

Thus, for instance, when using ferric chloride as ferric salt, this treatment may be carried out at 20-100° C until the chlorine content of the precipitate is reduced to values lower than 0.15% by weight.

The washed solid is then dried until its water content is reduced to a value of from 2 to 8% by weight, operating at a temperature not exceeding 120° C, possibly by gradually raising the temperature and generally for a period of from 5 to 15 hours.

The solid obtained in this manner consists essentially of crystalline iron molybdate and molybdenum trioxide in intimate mixture and said solid as reduced to granules with separation of granules having a size suitable for the use in fluidized bed (in general from 40 to 300 mesh).

The granules are then dried at a temperature not exceeding 300° C and for a period such as to ensure the practically complete removal of water.

It is convenient to gradually increase the temperature during this treatment.

According to another procedure, the anhydrous granular solid may be obtained starting from an aqueous suspension of the washed precipitate by means of a simultaneous treatment of drying and granulation in an apparatus of the spray-drier type.

In any case, the granular solid thus obtained is endowed with high mechanical characteristics, but it shows a poor selectivity in the oxidation process of methanol to formaldehyde.

The calcining of said solid at temperatures higher than about 400° C (for example at 420°-430° C) allows the selectivity characteristics to be improved, but adversely affects the mechanical characteristics, especially the hardness, rendering the resulting catalyst unsuitable for use in a fluidized bed.

Therefore, according to the present invention, the granular solid is impregnated with an aqueous solution of a decomposable bismuth salt, in such conditions as to ensure an amount of deposited bismuth, expressed as metal, of from 0.5 to 10% by weight with respect to the crystalline iron molybdate, and preferably of from 1.5 to 5% by weight.

Suitable bismuth salts for the purpose are those which are decomposed into oxide at temperatures higher than 260° C, such as, for example, bismuth nitrate $Bi(NO_3)_3.5H_2O$, and basic bismuth nitrate $BiONO_3.H_2O$.

The impregnated granules are then dried, generally at a temperature not exceeding 120° C, and are finally calcined. The calcining temperature should preferably not exceed 600° C, and is typically from 300° to 450° C. The calcining period should preferably not exceed 12 hours and is typically from 5 to 7 hours.

The calcining is preferably carried out at increasing temperatures which, however, are still in the indicated range of values.

It has been experimentally ascertained by differential thermal analysis that during this treatment at elevated temperature, an interaction occurs between the bismuth oxide which is deposited on the surface of the granules and the other constituents of the catalyst, such as, for example, the formation of bismuth molybdate.

In any case, operating in the described manner, a catalyst is obtained which is active and selective in the oxidation process of methanol to formaldehyde, and said catalyst is endowed with such mechanical characteristics as to render it suitable for use in a fluidized bed.

This catalyst shows no tendency to lose molybdenum trioxide in use on account of volatility. It should be noted that the treatment with bismuth compounds permits the selectivity characteristics of the catalyst to be improved without, however, adversely affecting the mechanical characteristics, especially the hardness.

Finally, it should be noted that the final calcining should preferably not exceed the indicated time and temperature limits in order not to excessively reduce the surface area of the catalyst and thus its activity.

In the following experimental examples, the hardness of the catalyst is measured by means of the following abrasion resistance test.

From 5 to 10 grams of catalyst screened to a size range suitable for fluidization are charged to a Pyrex glass tube (18 mm in diameter, 20 cm in length) connected at its lower end with a reservoir of compressed air.

The other end of the tube is provided with a small net having a hole diameter smaller than the size of the catalyst under examination.

A stream of air is then passed through the tube at the rate of 700-800 l/hr, the catalyst is fluidized and the fine powder formed by abrasion between the particles in motion is taken into suspension by the gaseous stream.

The tube is weighed at regular intervals of time and the weight loss percentage in catalyst is thus determined.

It has been found that said loss is a function of the amount of bismuth oxide deposited, as indicated below:

| % by weight of bismuth (as metal) with respect to the iron molybdate | weight loss percentage in catalyst per each 100 hr |
| --- | --- |
| 0.5 | 0.5 – 0.6 |
| 3.0 | 0.2 – 0.3 |
| 6.0 | ≈ 0 |

It should be noted that in the absence or bismuth oxide this loss is of the order of 0.7–0.8% by weight if the determination is effected on iron molybdate-molybdenum trixoide not submitted to calcination and of the order to 2–3% by weight, still in the absence of bismuth oxide, if the determination is effected on iron molybdate-molybdenum trioxide calcined at 400° C.

In order to give an idea of the hardness of the catalyst of the present invention, it may be noted that silica, in the same fluidization conditions, shows a loss of the order 0.001–0.01% by weight.

EXAMPLE 1

39.5 g of commercial ammonium paramolybdate $(NH_4)_6Mo_7O_{24} \cdot 4H_2O$ are dissolved in 1750 ml of distilled water and the resulting solution is brought to pH 1.18 by means of a concentrated aqueous solution of hydrochloric acid.

The solution is heated to 45° C and there are added 50 g of iron nitrate $Fe(NO_3)_3 \cdot 9H_2O$ dissolved in 350 ml of distilled hours.

The mass is maintained under agitation and at boiling point for 3 hours.

The hot suspension thus obtained is filtered on a Buckner funnel, the solid is washed on the filter with 350 ml of water acidulated with nitric acid.

The cake is reduced to slurry by adding 400 ml of boiling water and vigorously stirring for 5 minutes. The slurry is filtered and the wet cake is dried as such at 115° C for 12 hours.

37 g of a very hard crust having a pale green colour are obtained. This solid contains 25.3% by weight of $MoO_3$ with respect to the iron molybdate $Fe_2(MoO_4)_3$, and its chlorine content is lower than 0.15% by weight.

EXAMPLE 2

7.9 g of commercial ammonium paramolybdate are dissolved in 350 ml of distilled water, the solution is brought to pH 1.2 by means of a concentrated aqueous solution of hydrochloric acid, heated to 45° C, and 10 g of iron nitrate dissolved in 75 ml of water are then rapidly added. The mixture is then boiled for 4 hours under vigorous agitation.

The resulting suspension is filtered, thoroughly washed to remove the chlorine ions and the wet cake is dried as described in Example 1.

There is obtained a very hard crust olive green in colour. The molybdenum/iron atomic ratio in the solid is equal to about 2.1 : 1, which corresponds to 20% by weight of $MoO_3$ with respect to the iron molybdate.

EXAMPLE 3

39.5 g of commercial ammonium paramolybdate are dissolved in 1750 ml of distilled water and the solution is acidified by means of a 12.4 molar aqueous solution of hydrochloric acid to pH 1.25. After heating the solution to 45–48° C, 50 g of iron nitrate dissolved in 350 ml of distilled water are added in 2–3 minutes. A yellow precipitate is formed.

At this point about 1400 ml of limpid solution lemon-yellow in colour and containing some dissolved iron chloride are filtered off. The filtering operation is carried out in order to reduce the volume of the reacting mass.

The residual suspension after filtration is heated at boiling point for about 3.5 hours under vigorous agitation.

The suspension is then filtered on a Buckner funnel, the solid is washed on the filter with water acidulated by nitric acid, and the wet cake is reduced to slurry by addition of 500 ml of distilled water.

After 5 minutes of stirring at boiling point, the slurry is filtered, discharging with the filtrate the major part of the chlorine ions.

After drying a 115° C for 10 hours there is obtained a hard crust yellowish-green in colour, whose weight is about 38 g.

This solid contains 28% by weight of $MoO_3$ with respect to the iron molybdate.

EXAMPLE 4

39.5 g of commercial ammonium paramolybdate are dissolved in 1750 ml of distilled water and the resulting solution is acidified with 35.8 ml of nitric acid having a density of 1.4.

The solution is heated to 45° C and 33.5 g of ferric chloride $FeCl_3 \cdot 6H_2O$ dissolved in 350 ml of distilled water at ambient temperature, are added. The whole is rapidly mixed while maintaining the mass under agitation.

The mixture is filtered on a Buckner funnel, the filtercake is taken up two times with 500 ml of boiling distilled water while thoroughly mixing to remove any soluble salt present. After filtration, the wet cake thus obtained is oven dried at 115° C for about 10 hours.

35 g of a hard crust bright yellow in colour are obtained. The solid contains 27% of $MoO_3$ with respect to the iron molybdate.

EXAMPLE 5

10 g of the solid obtained in Example 1, ground and sifted to 52–60 mesh, are calcined at 300° C for 4 hours, taking care during the heating and the cooling that the rate of 5° C per minute is not exceeded.

The calcined product is charged into a flask in which it is possible to apply vacuum.

Maintaining a pressure of 1–2 mmHg, the catalyst is sprayed with 3.6 ml of a solution of 730 mg of bismuth nitrate $Bi(NO_3)_3 \cdot 5H_2O$ in nitric acid (acid dilution of 1:20). The flask is rotated in such a manner that the solution will wet the whole surface of the particles. The moist solid is dried at 110° C for 2 hours and then calcined at 305° C for 3 hours and finally at 430° C for 2 hours.

The catalyst thus obtained, when submitted to the abrasion test already described, after a loss of 0.2% by weight during the first 4 hours, loses in a regular manner 0.3% by weight over each 100 hours of fluidization.

The same catalyst, charged to a Carberry apparatus and contacted with a mixture of air with 6% of methanol by volume, at a temperature of 250° C and with a contact time of 1–1.5 seconds, allows the production of formaldehyde with a conversion of 93–95% with respect to the methanol and with a selectivity of 90%.

EXAMPLE 6

Two samples of the solid prepared according to Example 4, sifted to 60 mesh and calcined at 300° C for 7 hours, are respectively impregnated with a solution of $Bi(NO_3)_3 \cdot 5H_2O$ in $HNO_3$ (1:10 in volume) at a concentration of 13.7% by weight and with a similar solution at 27% by weight.

The amount of solution utilized is equal to 5.3 ml for each 10 g of calcined product.

The impregnated solid is kept at 110° C for 2 hours, at 305° C for 3 hours and at 430° C for 2.5 hours.

The two catalysts thus obtained, when submitted to the abrasion test, show respectively a loss of 0.3% and 0.02% by weight over each 100 hours of fluidization.

EXAMPLE 7

A sample of solid prepared as in Example 4, sifted at 60 mesh, is calcined at 300° C for 3 hours and impregnated with an aqueous solution of bismuth nitrate. The amount of salt $Bi(NO_3)_3 \cdot 5H_2O$ is equal to 7.5% by weight with respect to the solid submitted to treatment.

After impregnation calcining follows as in Example 5. The catalyst thus obtained shows a loss by weight equal to 1.08% after 400 hours of fluidization.

The catalysts prepared in Examples 6 and 7 are used for the oxidation of methanol to formaldehyde under the conditions described in Example 5.

There is obtained a conversion of methanol of the order of 95–97% with a selectivity for formaldehyde of the order of 93%.

EXAMPLE 8

An aqueous suspension at 30% by weight of the precipitate obtained according to Example 1, thoroughly washed to remove the water-soluble salts and the chlorine ions, is introduced to a commercial "Anydro" apparatus having a vaporizing capacity of 7 liters of water per hour. 5.5 l/hr of suspension are sprayed in by means of the centrifuge located at the top of the drying chamber; the drying air is delivered in equicurrent and a temperature of 320° C is noted at the inlet, whereas a temperature of 120° C is noted at the outlet.

A powder is obtained at the base of the recovery cyclon; screening shows that about 50% of this powder consists of granules of 50 microns, the remainder consisting of fine granules not smaller than 30 microns and of large size particles not exceeding 100 microns. A sample (20 g) of powder is impregnated with an aqueous solution of $Bi(NO_3)_3 \cdot 5H_2O$ as in Example 7 and calcined in the manner indicated in Example 5.

The catalyst thus obtained shows at the abrasion test a weight loss equal to 0.4% during the first 100 hours.

We claim:

1. A method for the preparation of a catalyst active and selective in the oxidation of methanol to formaldehyde and usable in the fluidized form in said oxidation, which comprises:
   a. mixing an aqueous solution of a soluble molybdate having a pH value of from 1.05 to 2.8 with an aqueous solution of a soluble ferric salt at a temperature of from 20° to 80° C in such proportions as to ensure in the resulting mixture an atomic ratio of molybdenum to iron of from 1.6:1 to 2.2:1, thereby to obtain a suspension of an amorphous precipitate;
   b. heating said suspension for at least 30 minutes at a temperature of from 70° C to its boiling point, thereby to transform said amorphous precipitate into crystalline iron molybdate and molybdenum trioxide;
   c. washing the resulting precipitate with water at a temperature from 20°–25° C to 100° C to remove the soluble salts produced;
   d. drying the washed precipitate at a temperature not exceeding 120° C, thereby to reduce its water content to a value of from 2 to 8% by weight;
   e. reducing the dried precipitate to granules and drying said granules at a temperature not exceeding 300° C to completely remove water;
   f. impregnating said granules with an aqueous solution of decomposable bismuth salt in such conditions as to ensure an amount of deposited bismuth expressed as metal of from 0.5 to 10% by weight with respect to the crystalline iron molybdate;
   g. drying said impregnated granules and calcining them at a temperature of at least 300° C for a period of at least 4 hours.

2. The method of claim 1, which comprises mixing an aqueous solution containing from 20 to 30 g/l of soluble molybdate with an aqueous solution containing from 90 to 140 g/l of soluble ferric salt.

3. The method of claim 1, wherein said aqueous solutions are mixed in such proportions as to ensure in the resulting mixture an atomic ratio of molybdenum to iron of from 1.8:1 to 2.0:1.

4. The method of claim 1, wherein stage (b) is carried out for a period of from 30 minutes to 6 hours.

5. The method of claim 1, wherein stage (b) is carried out for a period of from 3 to 6 hours.

6. The method of claim 1, wherein in stage (e) said dried precipitate is reduced to granules of from 40 to 300 mesh.

7. The method of claim 1, wherein stage (f) is carried out under such conditions as to ensure an amount of deposited bismuth, expressed as metal, of from 1.5 to 5% by weight with respect to the crystalline iron molybdate.

8. The method of claim 1, wherein said bismuth salt is selected from those which decompose into oxide at a temperature higher than 260° C.

9. The method of claim 1, wherein said bismuth salt is bismuth nitrate or basic bismuth nitrate.

10. The method of claim 1, wherein said impregnated granules are dried at a temperature not exceeding 120° C and then calcined at a temperature of from 300° to 600° C for a period of from 4 to 12 hours.

11. The method of claim 1, wherein said calcining of stage (g) is carried out at a temperature of from 300° to 450° C for a period of from 5 to 7 hours.

12. A non-supported catalyst active and selective in the oxidation of methanol to formaldehyde and usable in the fluidized form in said oxidation, consisting essentially of granules of crystalline iron molybdate and molybdenum trioxide in intimate mixture, the amount of molybdenum trioxide being of from 5 to 35% by weight with respect to the crystalline iron molybdate, said granules having on their surface an interaction product thereof with bismuth oxide deposited in an amount of from 0.5 to 10% by weight, expressed as metal, with respect to the crystalline iron molybdate.

13. The catalyst of claim 12, wherein said molybdenum trioxide is present in an amount of from about 19–20% by weight and said bismuth in an amount of from about 1.5–5% by weitht, expressed as metal, with respect to the 5l crystalline iron molybdate.

* * * * *